US010042892B2

(12) United States Patent
Clifford et al.

(10) Patent No.: US 10,042,892 B2
(45) Date of Patent: Aug. 7, 2018

(54) QUESTION ANSWER SYSTEM USING PHYSICAL DISTANCE DATA

(71) Applicant: International Business Machines Corporation, Armonk, NY (US)

(72) Inventors: Emmet R. Clifford, Dunstable, MA (US); Stuart J. Clifford, Beverly, MA (US); Robert E. Loredo, North Miami Beach, FL (US); Fang Lu, Billerica, MA (US); William M. Quinn, Lexington, MA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/678,338

(22) Filed: Aug. 16, 2017

(65) Prior Publication Data

US 2017/0344611 A1    Nov. 30, 2017

Related U.S. Application Data

(63) Continuation of application No. 15/651,361, filed on Jul. 17, 2017, which is a continuation of application No. 14/338,406, filed on Jul. 23, 2014, now Pat. No. 9,740,746.

(51) Int. Cl.
*G06F 17/30* (2006.01)
*G06Q 50/22* (2018.01)

(52) U.S. Cl.
CPC .... *G06F 17/30528* (2013.01); *G06F 17/3043* (2013.01); *G06F 17/3053* (2013.01); *G06F 17/3087* (2013.01); *G06F 17/30554* (2013.01); *G06F 17/30864* (2013.01); *G06Q 50/22* (2013.01)

(58) Field of Classification Search
None
See application file for complete search history.

(56) References Cited

U.S. PATENT DOCUMENTS

| | | | |
|---|---|---|---|
| 8,020,104 B2 | 9/2011 | Robarts et al. | |
| 8,417,000 B1 | 4/2013 | Mendis | |
| 8,805,406 B1 | 8/2014 | Casaburi et al. | |
| 8,868,550 B2 | 10/2014 | Doppelt et al. | |
| 9,146,923 B2 | 9/2015 | Kim et al. | |
| 9,514,190 B2 | 12/2016 | Clifford et al. | |
| 9,740,746 B2 | 8/2017 | Clifford et al. | |

(Continued)

OTHER PUBLICATIONS

List of IBM Patents and Patent Applications Treated as Related, Aug. 11, 2017. 2 pages.

(Continued)

*Primary Examiner* — Belix M Ortiz Ditren
(74) *Attorney, Agent, or Firm* — Jay Wahlquist (57) ABSTRACT

A question relating to an individual is received and context from the question is extracted. Subject matter criteria can be identified from the context of the question. A database containing history data that includes recorded positional data for physical objects relative to the location of the individual at the time of recording can be accessed and relevant physical objects from the history data can be identified based upon the subject matter criteria. A set of answers can be generated for the question from a corpus of data and ranked based upon the identified physical objects and physical distance between the individual and the relevant physical objects.

1 Claim, 6 Drawing Sheets

(56) References Cited

U.S. PATENT DOCUMENTS

| | | |
|---|---|---|
| 2007/0111754 A1 | 5/2007 | Marshall et al. |
| 2010/0299329 A1 | 11/2010 | Emanuel et al. |
| 2011/0035284 A1 | 2/2011 | Moshfeghi |
| 2012/0078938 A1 | 3/2012 | Davis et al. |
| 2014/0149372 A1 | 5/2014 | Sankar et al. |

OTHER PUBLICATIONS

Accelerated Examination Support Document, U.S. Appl. No. 14/976,120. Signed Feb. 17, 2016. 8 pages.
Forsyth et al., "Detecting Objects in Images", Computer Vision A Modern Approach, Second Edition, Chapter 17, pp. 519-530.
Mell et al., "The NIST Definition of Cloud Computing", National Institute of Standards and Technology, U.S. Department of Commerce, Special Publication 800-145, Sep. 2011. 7 pages.
Unknown, "Object Recognition", RoboRealm Vision for Machines, Copyright 2005-2014 RoboRealm. http://www.roborealm.com/help/Object_Recognition.php, 10 pages.
Clifford et al., "Question Answer System Using Physical Distance Data", U.S. Appl. No. 15/651,361, filed Jul. 17, 2017.

QUESTION ANSWER SYSTEM USING PHYSICAL DISTANCE DATA

BACKGROUND

The present disclosure relates to question and query answering computer systems, and more specifically, to computer systems that rank answers based upon physical distances between an individual and objects relating to a question or query.

Question answering (QA) systems can automatically answer questions, posed by individuals, using a corpus of data. The corpus of data can include a database containing a set of articles or even the global Internet. The question answering system can be configured to analyze text documents within the corpus of data to make inferences about the possible answers to the posed question. The results of the analysis can then be presented in the form of one or more answers. These answers can be ranked according to the confidence that the QA system has in the answer being correct and the most useful. The accuracy of the QA systems can be related to the size and complexity of the corpus of data, which can lead to the use of large and complex data sources.

SUMMARY

Certain embodiments are directed toward a computer implemented method that involves receiving a question relating to an individual; extracting context from the question; identifying subject matter criteria from the context of the question; accessing a database containing history data that includes recorded multimedia data that contains positional data for physical objects relative to the location of the individual and over a period of time during which the multimedia data was recorded; identifying, based upon the subject matter criteria, relevant physical objects from the recorded multimedia of the history data; generating a set of answers for the question from a corpus of data; ranking the set of answers based upon the identified physical objects and physical distance between the individual and the relevant objects; and providing the ranked set of answers.

Certain embodiments are directed toward a computer system that has one or more computer processor circuits configured to: receive a question relating to an individual; extract context from the question; identify subject matter criteria from the context of the question; access a database containing history data that includes recorded positional data for physical objects relative to the location of the individual at the time of recording; identify relevant physical objects from the history data based upon the subject matter criteria; generate a set of answers for the question from a corpus of data; rank the set of answers based upon the identified physical objects and physical distance between the individual and the relevant physical objects; and provide the ranked set of answers.

Embodiments of the present disclosure are directed toward a computer program product comprising a computer readable storage medium having program instructions embodied therewith, the program instructions executable by a computer to cause the computer to perform a method comprising: receiving a question relating to an individual; extracting context from the question; identifying subject matter criteria from the context of the question; accessing a database containing history data that includes recorded positional data for objects relative to the location of the individual at the time of recording; identifying relevant objects from the history data based upon the subject matter criteria; generating a set of answers for the question from a corpus of data; ranking the set of answers based upon the identified objects and physical distance between the individual and the relevant objects; and providing the ranked set of answers.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to question and answer (QA) systems, more particular aspects relate to QA systems that use object positional history data to rank answers. While the present disclosure is not necessarily limited to such applications, various aspects of the disclosure may be appreciated through a discussion of various examples using this context.

Embodiments of the present disclosure are directed toward a QA system that is designed to utilize individualized history data that is collected from a recording device that is kept proximal to an individual. In various embodiments, this data can be automatically collected without the individual's direct input. The data can include, but is not necessarily limited to, captured audio, video, photos and text. The QA system can analyze the data and rank the search results based on the physical distance between the individual (where the data was collected) and relevant subject matter of the question. The physical distance can be used to rank and filter answer results and/or filter or weight corpus data that is used to generate the answer results.

For example, particular embodiments may utilize data collected by a recording device that can be carried on an individual. This may include wearable recording devices, such as eyeglasses with video and audio recording circuits. It may also include portable devices that may be carried by an individual and that may have recording capabilities, such as smart phones or tablets. The multimedia generated by the recording device can be stored in a history database for the individual and possibly for other individuals also. The system can be configured to identify relevant subject matter based upon the question being asked. The relevant subject matter can then be correlated to the history data in order to determine relative distances between objects corresponding to the subject matter and the individual. This can be useful for filtering or reducing the search and analysis of the data corpus used to answer the question as well as for personalizing the answer to the asking individual.

As discussed herein, the history data can be retrieved for the individual asking the question. In various embodiments, however, the history data can be retrieved for the subject of the question, which may not be the same as the individual asking the question and which may include more than one individual. For example, a doctor may submit a question on behalf of a patient, or set of patients. The QA system can be configured to access history data for a patient, assuming the QA system can verify that the patient has granted such access to the doctor. Moreover, questions might be automatically generated by another computer system on behalf of an individual. Accordingly, while the history data is often discussed herein with regards to the asking individual, it is understood that the history data may be for a different individual than the asking individual.

Consistent with embodiments, the relative distances between corresponding objects and the individual can be used to rank answers to the question. For example, an individual may ask a question regarding a health issue that can be caused by environmental factors, the answers can be ranked according to the relative proximity of objects associated with the environmental factors. In addition to proximity, the total amount of time and frequency an object is proximal to the individual can be factored into the ranking.

Figure 1:
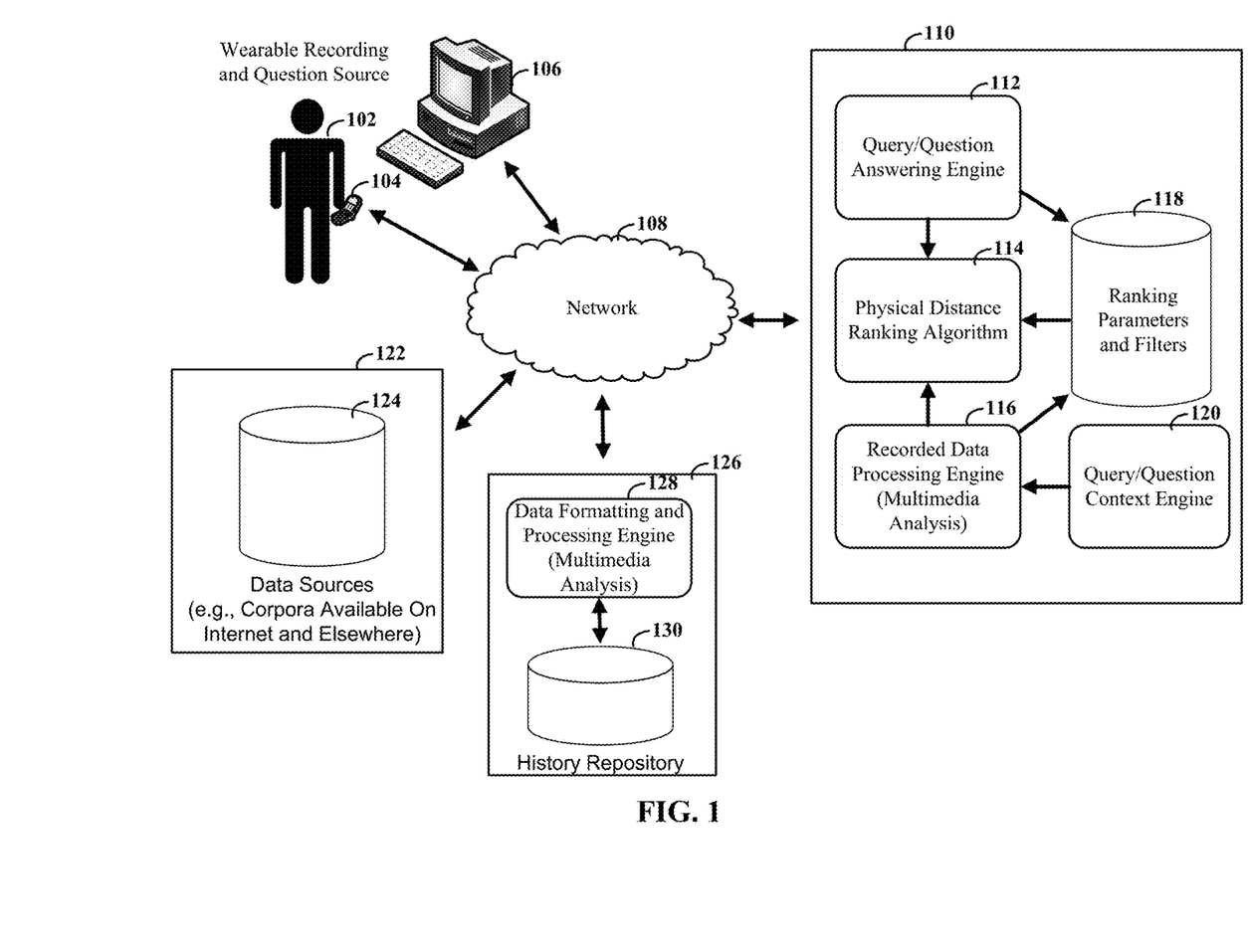
FIG. 1 depicts a system for generating answers based upon history data that contains proximity information, consistent with embodiments of the present disclosure.

Turning now to the figures, FIG. 1 depicts a system for generating answers based upon history data that contains proximity information, consistent with embodiments of the present disclosure. An individual 102 can carry or wear one or more recording devices 104. For example, a wearable recording devices could be used to record video, audio, still images, and combinations thereof. A few examples of wearable devices that also have recording functions include glasses, watches and headsets. Other possible recording devices include portable devices, such as smart phones, cameras, and tablets. Recording devices other than those expressly mentioned are also possible for inclusion. The multimedia recorded by the wearable device can be obtained over varying periods of time (e.g., hours, days, or even longer).

A computer (server) device 126 can be configured to collect and store recorded history data in a user history repository (or database) 130. In certain embodiments, the data can be received over one or more networks 108. The networks can include, but are not limited to, local area networks, point-to-point communications, wide area networks, the global Internet and combinations thereof. The computer devices and processors discussed herein can include one or more computer processor circuits and storage circuits that can be configured to perform various functions and provide various modules, tools and engines. Moreover, the computer devices can be a single hardware platform or a group of multiple hardware platforms that are part of a distributed (virtual) environment.

Consistent with embodiments, the recorded history data can be stored with a user identification so that the user history repository 130 can store history data for multiple individuals. In certain embodiments, a separate history repository 130 can be created for each individual. In some embodiments, the computer device 126 can optionally include a data formatting and processing engine 128. The engine 128 can be configured to analyze recorded multimedia data in order to identify and parse information from the multimedia data. For instance, the engine 128 could perform optical character recognition (OCR) of image data in order to identify text. The identified text could then be stored in the history repository 130 along with the image data. The processing engine could also perform other analysis, such as identifying objects in images, or identifying the source of sounds in an audio recording. Another function of the engine 128 could be determining a distance between identified objects and the recording device or the individual using the recording device.

An individual that has built up a history record in history repository 130 can submit a question using a computer device 106 (e.g., a personal computer, laptop computer, smart phone, tablet or other network capable device). This question can be directed through network 108 to a question and answer (QA) computer server 110. Along with the words of the question, QA server 110 can also receive identifying information about the individual asking the question. This information can be used to generate a query for the individual that is designed to retrieve corresponding data stored in history repository 130.

According to embodiments, the QA server 110 can use a query/question answering engine 112 to develop a set of possible answers to the questions. The QA engine 112 can develop these answers using data obtained by querying one or more data sources 124, which can be stored locally on QA server 110 or remotely on other computer servers 122. Data sources 124 can include a number of different corpora of data, which can be available on the global Internet or elsewhere. For example, the data can be retrieved from sources that might include journal publications, electronic libraries, online forums, websites, and Internet search engine results.

In certain embodiments, the QA server 110 can determine the subject matter and context of the question using a query/question context engine 120. This may include applying one or more natural language processing (NLP) algorithms to the question in order to determine the context of the question. NLP can be used to develop an understanding of human languages by a computer. They can allow a computer to be convert normal human language into data that the computer normally processes. In dealing with a written language, one problem is ambiguity: incomplete information, contextual information, etc. An NLP algorithm may perform one or more of morphological analysis, syntactical analysis or parsing, semantic analysis, or pragmatic analysis. In morphological analysis, the NLP algorithm can analyze individual words and punctuation to determine the part of speech the words with or without punctuation are (or could be). In syntactical analysis or parsing, the NLP algorithm can determine the sentence constituents and the hierarchical sentence structure, using word order, number agreement, case agreement, and/or grammars. In semantic analysis, the NLP algorithm can determine the meaning of the sentence. To deal with sentence ambiguity, the NLP algorithm may look to the specific actions being performed on specific objects. In pragmatic analysis, the NLP algorithm can determine an actual meaning and intention in context (of speaker, of previous sentence, etc.). The NLP algorithm can be configured to handle pronouns such as "it," to identify implicit meanings. To handle all this, the NLP algorithm may keep track of the focus of the dialog, a model of each participant's beliefs, as well as knowing the rules and goals of dialog.

Thus, in accordance with certain embodiments, NLP can be used to identify contextual information for a given question through morphological analysis, syntactical analysis or parsing, semantic analysis, pragmatic analysis and combinations thereof. For example, context may be derived by identifying parts of speech, such as nouns, pronouns, verbs, adverbs, adjectives, prepositions, conjunctions, interjections, or the like, prepositional phrases, clauses, indefinite terminology, or the like, sentence constituents and the hierarchical sentence structure, sentence meaning, actual meaning, intention in context, or the like.

Based upon the context of the question, the question context engine 120 can identify one or more objects of relevance. For example, if the question pertains to a skin irritation or rash, the context engine might identify objects that are potential allergens (e.g., foods, soaps, lotions, and pets). In certain embodiments, the objects can be identified by first searching one or more of the available corpora of data. Based upon the search results, one or more objects can be identified. For example, the context engine 120 may determine that the question subject matter relates to the medical condition of insomnia. A search of a medical database may identify possible causes as including stimulating activities (e.g., television), medications, stimulants (e.g., caffeine or nicotine) and others. A list of objects that relate to one or more of these possible causes could then be generated. In some instances, the context engine 120 could do a subsequent search to identify possible objects (e.g., search for a list of stimulants and/or their sources).

A recorded data processing engine 116 can be configured to analyze the recorded history data for the individual based upon the list of objects and subject matter criteria. For example, the processing engine 116 can be configured to analyze different forms of multimedia to find matches with the identified objects. This may include optical character recognition (OCR), which might be used, in the insomnia question context, to read the contents of medications or food. It may also include object recognition algorithms that can identify objects in a picture or a video clip. Audio clips can also be analyzed (e.g., identifying that a television that is on in the same room). The processing engine can then also determine an estimated distance between the identified objects and the recording device or individual.

As discussed in connection with computer device 126, some of this type of data processing and analysis can be performed before a question is presented, which can help make the process more efficient. For instance, the processing engine 128 can be configured to identify a variety of general objects (without knowledge of the question) and store this information in the database. Once a question is received, processing engine 116 can be configured to search for, and identify, any additional objects that have not already been identified by processing engine 128.

A physical distance ranking algorithm 114 can then be used to rank the answers from QA engine 112 based upon the identified objects and their respective distances from the asking individual. For instance, a person may have submitted a question relating to wrist pain. The results may include a large number of possible causes, each cause representing at least one possible answer. The ranking algorithm 114 can rank the answers by first presenting objects that were identified as being in contact with the hand or arm and that are also found within the potential answers. This can be particularly useful for providing a set of ranked answers that are tailored to each individual's personal recorded history. In the case of wrist pain, a first individual may have answers relating to a computer mouse has a high ranking due to the recorded history indicating close proximity between the mouse and the individual's hand (as well as the frequency and duration of the proximity). A second individual submitting the same question, however, may have answers relating to a gardening tool as a high ranking due to the recorded history indicating a close proximity to the tool (also considering the frequency and duration of the proximity).

In certain instances, the ranking algorithm 114 can be configured to rank answers strictly based upon relative distances. This may work well for answers in which the distance is the dominating factor (e.g., where the various objects have relatively equal relevance to the question). As an example, a question may inquire about the source of a bruise on a person's arm. All hard objects can be listed in relative order to their detected physical proximity to the location of the bruise.

In various instances, other factors can be considered by the ranking algorithm 114. This may be useful for situations where, for example, the duration of the proximity is relevant. These and other factors can be adjusted using a set of ranking parameters and filters 118. In some instances, the ranking parameters and filters 118 can be adjusted based upon determinations from the QA engine 112 and the processing engine 116. For example, the QA engine can be configured to identify relevant parameters for ranking based upon the various answers. These parameters and filters can include, but are not limited to, duration of proximity, thresholds filters for proximity (e.g., relevance increases once an object is less than a foot away), relevance of object motion (or lack thereof), and time of day relevance (e.g., higher relevance in the evening or night for insomnia). Similarly, the recorded data processing engine 116 could identify and modify parameters based upon objects that were identified or other information from the stored history data.

Once the physical distance ranking algorithm 114 has determined the ranking for the answers, the ranked answers can then be displayed to the asking individual using computer device 106. In certain embodiments, the asking individual can be presented with an option to enable or disable the physical proximity sorting. Other embodiments allow for two different lists to be displayed simultaneously, one with physical proximity sorting enabled and one without.

Figure 2:
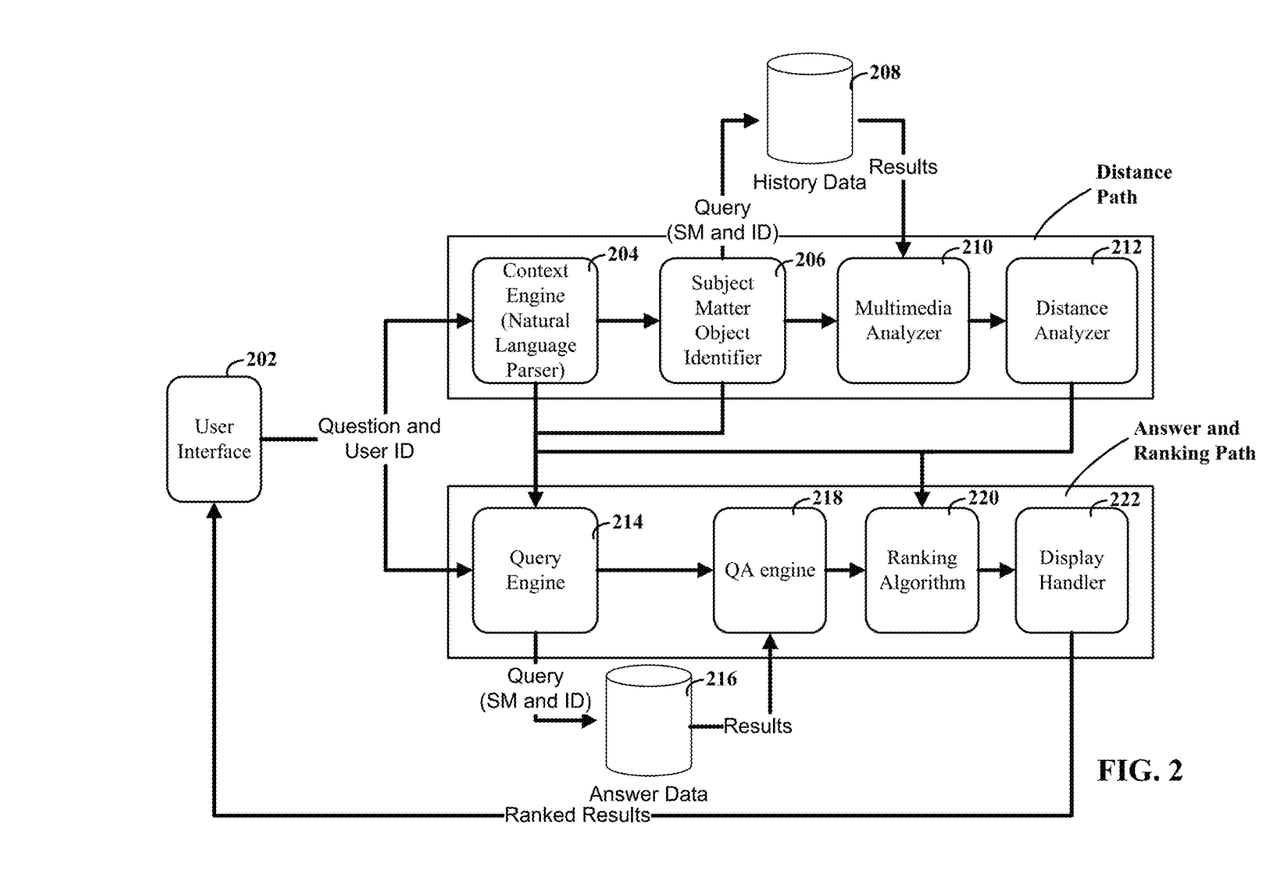
FIG. 2 depicts a flow diagram for generating ranked answers using physical distance history data (or proximity history data), consistent with embodiments of the present disclosure.

FIG. 2 depicts a flow diagram for generating ranked answers using proximity history data, consistent with embodiments of the present disclosure. An individual seeking an answer to a question can access a user interface 202. In some instances, the user interface 202 can be generated from a dedicated QA interface program. In other instances, the user interface 202 can be generated within a generalized application, such as a web browser, that retrieves the user interface details from a remote server.

Consistent with embodiments, the user interface 202 can be configured to also receive user identification (ID) information about the person asking the question. For instance, the user might provide a login ID and password to confirm their identity. The question and user ID can then be provided the QA system. As depicted, the flow diagram can proceed along two different paths, a distance path and an answer and ranking path. Although, the paths are depicted as separate logical paths that can be carried out using separate hardware components and software platforms, various embodiments allow for the paths to be carried out on the same set of hardware devices and within a common software platform. Moreover, the different paths can have varying levels of interrelationships.

Consistent with certain embodiments, a context engine 204 can analyze the user question in order to determine the general subject matter of the question. For example, the context engine 204 can be configured to employ one or more natural language processing algorithms in order to infer content and context for the question. This might include, for example, using a key word extraction and parsing analysis along with a question classification to identify probably subject matter relevance for different objects. The subject matter identified through such analysis can then be provided to the subject matter object identifier module 206. The identified subject matter can also be used by the query engine 214, which is shown as part of the answer and ranking path.

As an example, two questions posted in an Internet forum could be: Q1: What are the steps in order to start my server? Q2: What are the steps in order to start my email server? The context engine 204 could identify context of both of these questions as "starting a server."

As discussed herein, such context can be identified using one or more NLPs. For example, NLPs can parse and analyze unstructured or structured textual content of questions in a variety of ways in order to identify semantic and syntactic elements within the text. The identified elements can then be used to identify the context of the question as a function of the organization and structure of the question syntax. The NLP analysis can be based upon, but is not limited to, parts of speech, keywords, sentence structure information, focus, lexical answer type and synonyms. These components can form part of the context of the question.

Using such NLP techniques, along with other text mining techniques, contextual information can be identified. Once the contextual information is identified, it can be extracted and used by the system. In the previous example questions, the system can identify words (or entities) of the sentence that have perceived signification (in this case, the words: steps, order, start, and server might be selected) and then use NLP to determine (e.g., based on the order of the words in the sentence) a particular context.

Once context for a question has been identified, the system can match the context to a repository or list of subject matter experts (e.g., users/profiles in online forums) in order to filter, or select, specific data from the available repository data. For example, based upon the context, the system can create filter parameters for expert's profile information. The system can then filter out posts by individuals lacking sufficient technical background (e.g., schooling or years of industry experience). For example: for Q1, the system could search for profiles of individuals that have experience in servers and then use the content of posts by these individuals to generate answers. For Q2, the system could be more specific and identify profiles of individuals with experience in email servers and then use the content of posts by these individuals to generate answers. The answers can then be filtered and sorted based upon proximity information derived from the history data.

In certain embodiments, the system can supplement and determine context based upon an analysis of the history data. In the case of the example questions Q1 and Q2, the system could search the history data of the asking individual for images that depict servers in physical proximity to the individual. The system can then identify text in the images that contains relevant information, such as identifying the type of computer and server hardware that has been in physical proximity to the individual asking the question. This may include the use of OCR to identify brand and model numbers from servers in the images.

In certain embodiments, a rating for subject matter experts can be defined either by a user or by other sources (e.g., automated ratings). This rating can be used to specify which data is used from an available corpus of data, as well as to weight data based upon the source of the data. For example, threshold values for number of years of experience and the level of knowledge based on product or industry experience can be used to filter the data from a corpus of data (e.g., by only including forum posts from experienced individuals). The filter data can then be used by the QA system to infer a list of possible answers to the questions.

The subject matter object identifier module 206 can associate the identified subject matter with one or more objects that may have been recorded and stored as part of the history data 208. For instance, the context engine may identify the subject matter as relating to brands of footwear. The object identifier module 206 may identify different objects relevant to different types of footwear, which might lead to an inference as to the particular needs of the individual. For instance, if the individual is often near heavy equipment associated with construction, this may result in a different set of answers (e.g., steel toe boots) than if the individual is often near objects associated with a particular sport (e.g., athletic shoes). A query for identified objects can then be generated to obtain information from the history data.

In response to such a query, multimedia analyzer 210 can retrieve information about the identified question subject matter and associated objects from the stored history data 208. In the Q1 and Q2 question examples, the objects might include computer hardware, computer monitors or other objects related to computer servers. This information can then be used to perform an analysis of the stored history data 208. In some embodiments, the query can request all data for the identified user. The system can also be configured to tailor the query based upon the identified subject matter, the identified objects, or other information. For instance, the query could be limited to particular time of day for certain subject matter. The output of the multimedia analyzer can include data about the presence (or absence) of objects that may be relevant to the question. For example, if a relevant object is a computer mouse, then the multimedia analyzer can detect whether or not a computer mouse was found in any of the images stored in the history data. In addition, a distance analyzer module 212 can be configured to determine a distance between objects and the individual. For example, if a computer mouse is identified as a relevant object, the distance analyzer module 212 can estimate the distance between the mouse and the individual from captured images stored in the history data 208. The data relating to relevant objects, including both the presence and distance, can be used in the answer and ranking path.

In particular embodiments, the query engine 214 can generate queries (directed toward answer data corpora 216) that include search terms that are generated from objects identified in the distance path. This can be particularly useful for situations where the data corpora 216 are particularly large. Search, load and analysis of large amounts of data can consume a significant amount of resources. For example, the data corpora 216 can contain a large amount of data from popular data repository such as encyclopedias, dictionaries, thesauri, newswire articles, and literary works. It may consume a significant amount of resources and time to receive and process the data returned from such large repositories. The distance (ad-hoc) data collected from the user, and possibly additional input from the user, can be used to filter and efficiently rank the search results. Accordingly, a first search can filter, or limit, the search results based upon the data received from the distance path.

QA engine 218 can use the results to generate a set of answers to the question. A few non-limiting examples of QA solutions include systems that: use hypothesis generation and evaluation to parse relevant evidence and evaluate responses from disparate data, use natural language processing that can allow for analyzing unstructured data, analyze structured data, track user feedback to learning from successes and failures, and combinations thereof.

Once a set of answers has been generated, ranking algorithm 220 can then rank the answers based upon the physical distance between an object associated with a particular answer and the asking individual. In the example question relating to wrist pain, this might include ranking answers relating to a computer mouse higher when the system determines that the distance between the asking individual and the computer mouse is small over an extended period of time. Consistent with various embodiments, the ranking can include additional parameters and associated algorithm(s). For instance, the ranking can be based upon the time of day that the physical distance is measured if the question infers relevance of time to the answer. For example, the time of day may be relevant for a question dealing with insomnia. The system might look for relevant objects (e.g., bright lights or possible sources of stress) that are near the individual at nighttime.

Display handler 222 can be configured to provide an interface between the answer and ranking path and the user interface 202. For instance, if the QA system is accessible through a website, the user interface 202 might include a web browsing software application. The display handler 222 can generate data for viewing within the web browsing software application. Consistent with embodiments, the display handler can also provide options for the user to provide feedback on the answers and to enable or disable the physical location/distance ranking option. When disabled, the distance path can be effectively bypassed and the QA system can answer the question(s) without using data from the distance path.

Figure 3:
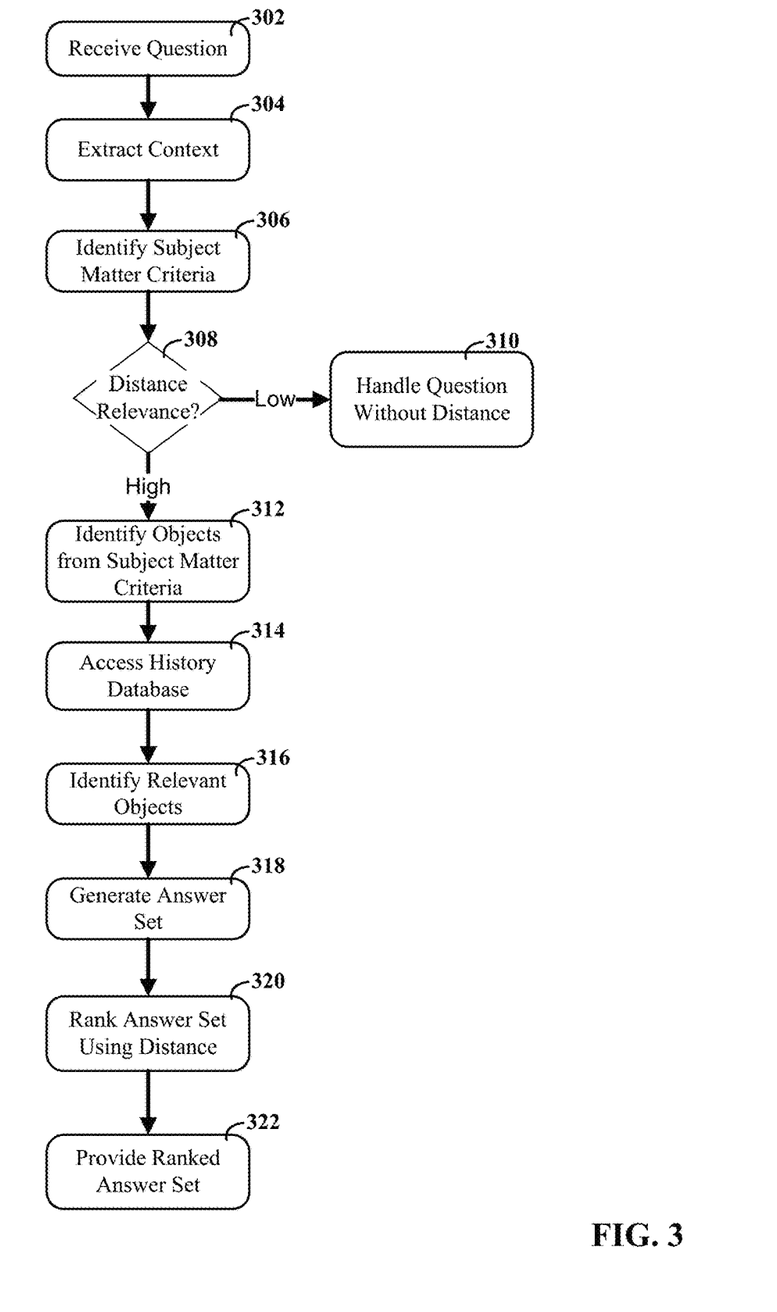
FIG. 3 depicts a flow diagram for generating a set of answers using physical distance data, consistent with embodiments of the present disclosure.

FIG. 3 depicts a flow diagram for generating a set of answers using physical distance data, consistent with embodiments of the present disclosure. The flow begins when a question is received from an individual, as shown by block 302. Consistent with embodiments, the question can be submitted using a website, mobile software application, dedicated software application or other interface options. As discussed herein, the question can include, or be associated with, an identity of the individual (user ID). For example, the individual may log into the system using a login ID and password. As discussed herein, this ID can then be used to retrieve previously stored history data for that individual.

The QA system can then extract context from the question, per block 304. This can include language parsing and analysis to convert the text of a question into a form that can be understood by a computer. From the extracted context, the system can identify the relevant subject matter criteria, per block 306. The relevance subject matter criteria can include information about whether or not objects, and their proximity to the individual, could be relevant to the question. This may also include information about the general type of objects or subject matter that is relevant. For example, a question relating to an allergic reaction may result in the identification of a subject matter criteria that identifies relevant categories of objects as including any flowering plant or animals with fur.

According to certain embodiments, the QA system can assess whether or not the subject matter criteria indicates that the proximity or distance to objects is relevant to the question, per block 308. In particular embodiments, this assessment can be made using a scale, or percentage, that indicates a determined likelihood that the proximity information will be relevant. In some embodiments, this assessment can be refined and adjusted based upon updated data that may include feedback from users of the QA system and also information in the corpus of data used to answer questions. In some instances, the distance relevance can include indications from a particular user as to whether or not distance ranking is desired. For example, a user can select whether or not distance ranking is enabled when submitting the question, or the user can have a set of user preferences that the QA system can refer to in the assessment.

If the QA system determines that the distance relevance is relatively low, e.g., below a threshold level or zero, then the QA system can handle the answer determination and ranking without using the distance or proximity data, as shown in block 310. If, however, the QA system determines that the distance relevance is relatively high, e.g., above a threshold level, then it can use the distance information by proceeding with the identity of objects, as shown by block 312. Some embodiments allow for the use of different threshold levels for different users or different subject matter areas. For example, the QA system can be configured with a threshold level for medical subject matter that is lower (and results in the use of more distance data) than a threshold level for weather-related subject matter.

The identification of objects from the subject matter criteria, per block 312, can be accomplished using a variety of different approaches. For example, the objects can be identified by search results from a corpus of data. The search can be of limited scope based and specifically tailored to the purpose of identifying objects (e.g., as opposed to analyzing the search for the purposes of answering the question). For example, a search of a medical database can be undertaken using key words associated with symptoms in a question. The results can be analyzed to find the frequency at which objects, that can be identified and would be recorded, appear in the database.

The identification of objects may use, for example, language parsing and/or natural language processing algorithms to identify subject matter of the question. In addition to identifying explicit terms and words within the text of a question, the QA system can expand the relevant object list based upon inferences and relationships between the question text and other terms and subject matter. For example, a question that relates to hand pain may result in the QA system creating an inference to objects that are associated with repetitive hand motions.

The QA system can then access a history database for the asking individual, as shown in block 314. This can include retrieving recorded multimedia that can include, but is not necessarily limited to, video, still images, audio and text (e.g., created from OCR). Moreover, metadata information can be accessed. This metadata may be associated with the multimedia including, but not limited to, date, time of day and geographic location.

The QA system can then analyze the accessed multimedia/history data in order to identify objects that were recorded as being proximal to the individual, per block 316. As discussed herein, the QA system can be configured to search specifically for objects that were previously identified. Moreover, in certain embodiments, the QA system can be configured to identify objects other than those previously identified. In addition to the identification of the object, the QA system can determine an estimated distance between the identified objects and the individual and/or the recording device.

The QA system can then generate a set of answers using the retrieved history data, information from the analysis of the history data, and data from the available corpora of data, as shown in block 318. Per block 320, the QA system can rank the answer set based upon the distance data and the identified objects. This set of ranked answers can then be provided to the asking individual, per block 322.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
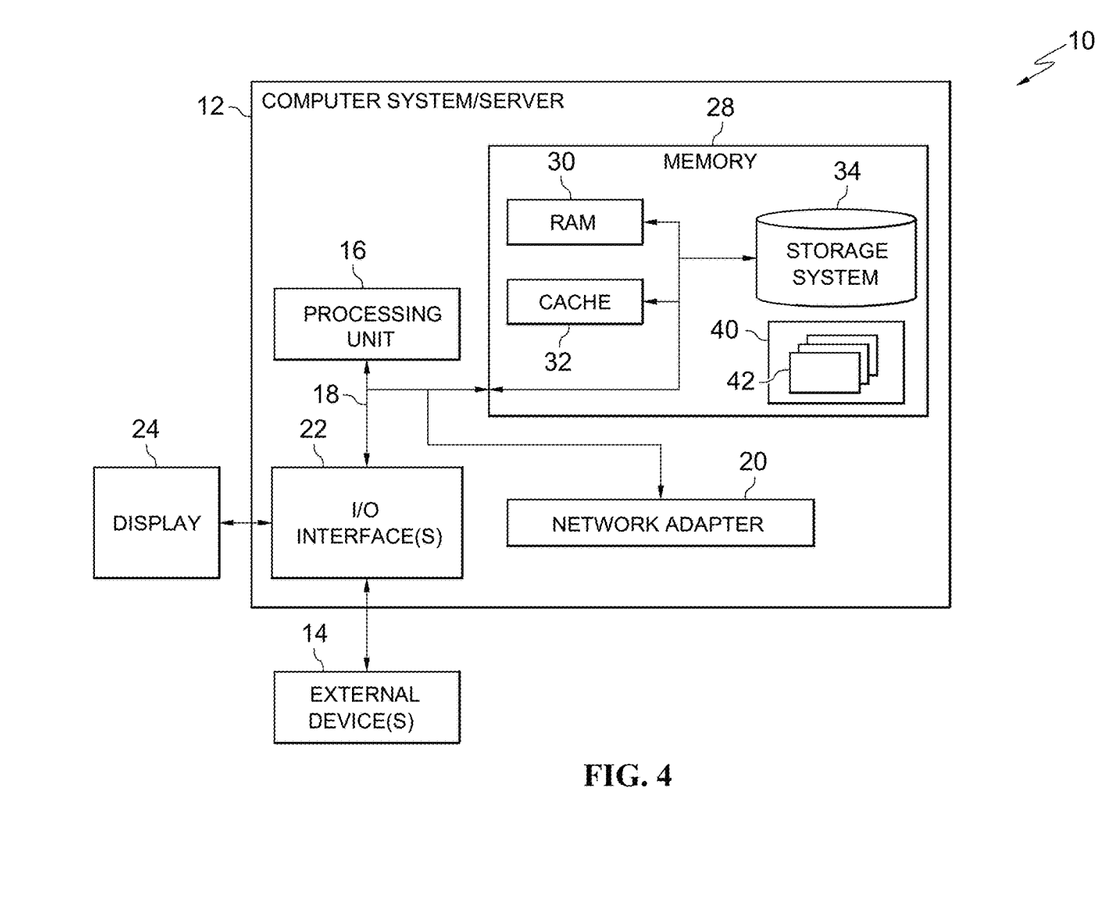
FIG. 4 depicts a cloud computing node, according to embodiments of the present disclosure.

Referring now to FIG. 4, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 5:
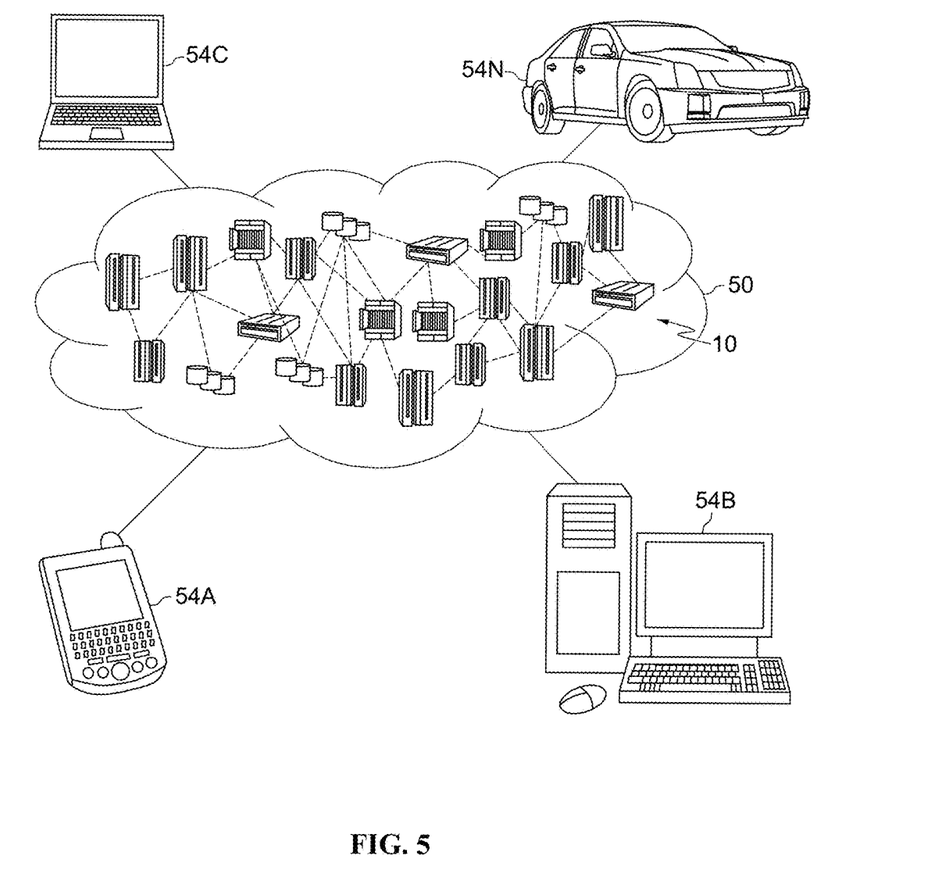
FIG. 5 depicts a cloud computing environment, according to embodiments of the present disclosure.

Referring now to FIG. 5, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
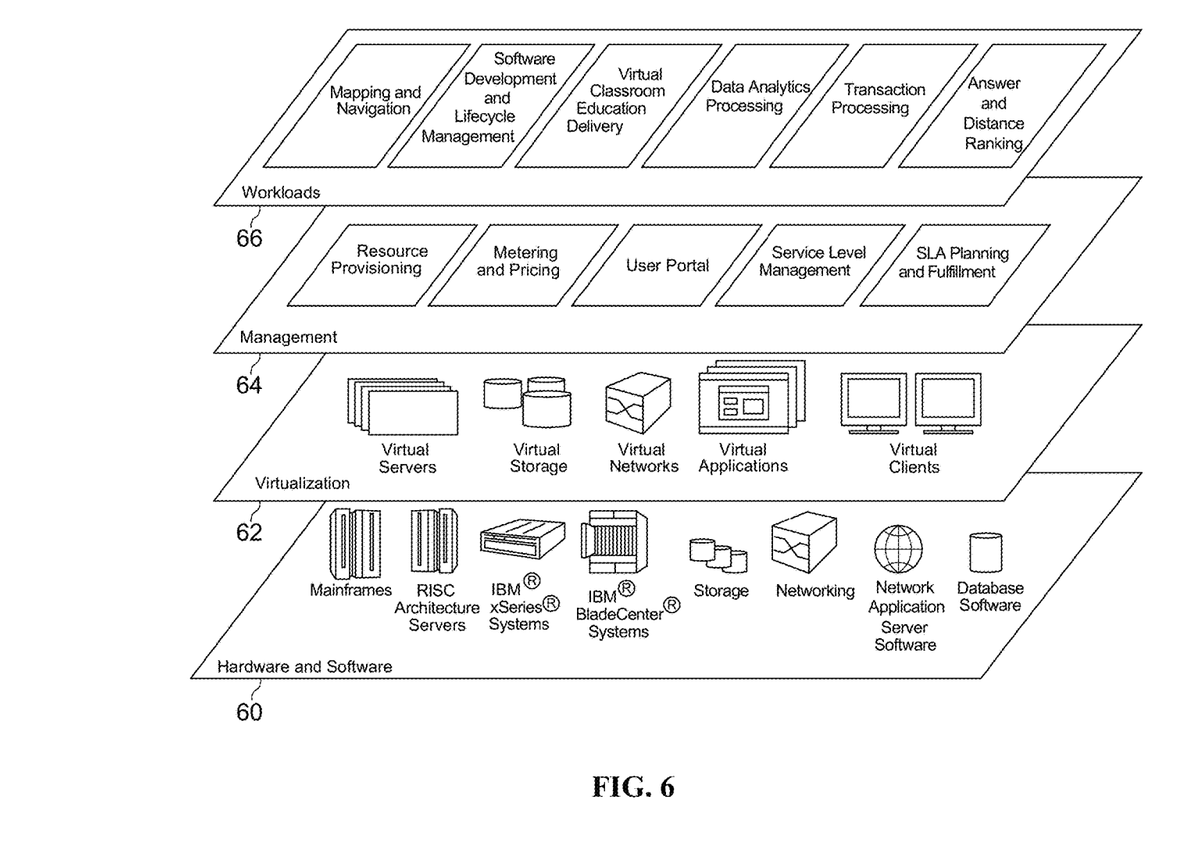
FIG. 6 depicts abstraction model layers, according to embodiments of the present disclosure.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 62 provides an abstraction layer from which the following examples of virtual entities may be provided: virtual servers; virtual storage; virtual networks, including virtual private networks; virtual applications and operating systems; and virtual clients.

In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; and transaction processing; mobile desktop; and QA systems with distance-based ranking.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A system comprising:
a memory; and
a processor coupled to the memory, wherein the processor is configured to:
receive a question associated with a user ID;
extract context from the question;
identify subject matter criteria from the context of the question, wherein the subject matter criteria includes information that indicates categories of objects relevant to the question and a determined likelihood that proximity information is relevant to the question;
compare the determined likelihood to a threshold;
in response to determining that the determined likelihood exceeds the threshold, access a history database associated with the user ID which contains history data obtained over a period of time using a wearable device worn by a user and that has video recording capabilities and audio recording capabilities, the history data including multimedia data that contains positional data for a plurality of physical objects, wherein the positional data indicates the respective physical distance between the plurality of physical objects and the wearable device when the multimedia data was collected;
identify one or more physical objects from the plurality of physical objects that are relevant to the question based upon the subject matter criteria and the history data;
generate a set of answers for the question from a corpus of data, each answer in the set of answers associated with a respective one of the one or more relevant physical objects;
rank the set of answers based upon the respective physical distance, at the time the multimedia data was collected, between the wearable device and the respective physical object associated with each answer in the set of answers, respective total amount of time each respective physical object was proximal to the wearable device, and respective frequency each respective physical object was proximal to the wearable device; and
display the ranked set of answers such that answers associated with a respective physical object having the smallest physical distance, at the time the multimedia data was collected, between the wearable device and the respective physical object are displayed first.

* * * * *